United States Patent
Smith

(10) Patent No.: US 6,950,190 B2
(45) Date of Patent: Sep. 27, 2005

(54) SCATTEROMETRY FOR JUNCTION METROLOGY

(75) Inventor: Walter Lee Smith, Danville, CA (US)

(73) Assignee: Therma-Wave, Inc., Fremont, CA (US)

(*) Notice: Subject to any disclaimer, the term of this patent is extended or adjusted under 35 U.S.C. 154(b) by 297 days.

(21) Appl. No.: 10/339,147

(22) Filed: Jan. 9, 2003

(65) Prior Publication Data

US 2004/0136003 A1 Jul. 15, 2004

(51) Int. Cl.$^7$ .............................................. G01N 21/47
(52) U.S. Cl. ..................................................... 356/446
(58) Field of Search ........................... 356/237.1–237.4, 356/445–448; 700/121, 117; 438/5–14

(56) References Cited

U.S. PATENT DOCUMENTS

| | | | |
|---|---|---|---|
| 4,579,463 A | 4/1986 | Rosencwaig et al. | 374/57 |
| 4,636,088 A | 1/1987 | Rosencwaig et al. | 374/5 |
| 4,854,710 A | 8/1989 | Opsal et al. | 356/432 |
| 5,607,800 A | 3/1997 | Ziger | 430/8 |
| 5,739,909 A | 4/1998 | Blayo et al. | 356/369 |
| 5,798,837 A | 8/1998 | Aspnes et al. | 356/369 |
| 5,867,276 A | 2/1999 | McNeil et al. | 356/445 |
| 5,963,329 A | 10/1999 | Conrad et al. | 356/372 |
| 5,978,074 A | 11/1999 | Opsal et al. | 356/72 |
| 6,383,824 B1 | 5/2002 | Lensing | 438/14 |
| 6,429,943 B1 | 8/2002 | Opsal et al. | 356/625 |
| 6,451,621 B1 * | 9/2002 | Rangarajan et al. | 438/14 |
| 6,458,605 B1 * | 10/2002 | Stirton | 438/7 |
| 6,660,543 B1 | 12/2003 | Stirton et al. | 438/16 |
| 6,697,153 B1 * | 2/2004 | Wright et al. | 356/237.4 |
| 6,806,951 B2 * | 10/2004 | Wack et al. | 356/237.2 |
| 6,823,231 B1 * | 11/2004 | Bode et al. | 700/121 |
| 2002/0038196 A1 | 3/2002 | Johnson et al. | 702/179 |
| 2002/0151092 A1 | 10/2002 | Li et al. | 438/16 |
| 2003/0223066 A1 * | 12/2003 | Lee et al. | 356/401 |
| 2003/0224261 A1 * | 12/2003 | Schulz | 430/22 |

OTHER PUBLICATIONS

Z.L. Wu et al., "Laser modulated scattering as a nondestructive evaluation tool for optical surfaces and thin film coatings," *Part of the Symposium on Laser–Induced Damage in Optical Materials:* 1998—Boulder, Colorado, SPIE, vol. 3578, Sep.–Oct. 1998, 9 pages in length.

Z.L. Wu et al., "Single–beam photothermal microscopy—a new diagnostic tool for optical materials," *Part of the Symposium on Laser–Induced Damage in Optical Materials:* 1998—Boulder, Colorado, SPIE, vol. 3578, Sep.–Oct. 1998, 10 pages in length.

* cited by examiner

Primary Examiner—Michael P. Stafira
(74) Attorney, Agent, or Firm—Stallman & Pollock LLP

(57) ABSTRACT

The use of scatterometry measurements is proposed for the evaluation of the implantation or annealing of dopants in a semiconductor. In accordance with the subject method, a probe beam of light illuminates the wafer having the dopants implanted therein. The light reflected from the sample is measured and subjected to a scatterometry analysis. The information derived is correlated to the implant region so that parameters of the implant, such as depth of a junction and lateral spreading of the implant or the dose of implanted ions can be evaluated.

13 Claims, 4 Drawing Sheets

SCATTEROMETRY FOR JUNCTION METROLOGY

TECHNICAL FIELD

The subject invention relates to the use of scatterometry to evaluate dopants after implantation in a semiconductor wafer.

BACKGROUND OF THE INVENTION

Many modern technologies rely on the modification of surface material properties by physical and chemical processes to achieve particular surface characteristics. Some of these modification methods are applied broadly over an entire surface, such as the nitridation hardening of metal parts for use as drill bits or automotive engine valves. In these cases, it is important to know the variation of the modification from the surface into the bulk of the material along the vertical dimension. Another example, shown in FIG. 1, is the formation of an electrical junction in a silicon wafer by ion implantation and rapid thermal annealing. Modification methods can also be applied in a localized manner, such as the ion implantation of semiconductor materials through a sub-micron-scale patterned mask to produce localized circuit elements or "features" (see FIG. 2). The ion-implanted wafer is subsequently annealed to activate the dopant. In the localized cases, it is important to know the variation of the modification from the surface into the bulk of the material along the vertical dimension, and also to know the lateral variation of the modification across the transition from masked (not implanted) to non-masked (implanted) locations. The modification variation along the vertical (z) and lateral (x,y) dimensions can be termed the modification profile $M(x,y,z)$. The total modification per unit area $M_0(x,y)$ produced in the wafer can be obtained by numerical integration over z. In the case of ion implantation, $M_0(x,y)$ is the total damage from the ion implantation and can be related by calibration to the dose of implanted ions.

For integrated circuit (IC) fabrication, localized regions of different resistivity are created in a silicon chip (wafer) by first creating a pattern or mask using well-known photolithography methods (FIG. 2). The mask material may be photoresist or SiO2, Si3N4, or any other material that will block the passage of the dopant. The modifier elements are then caused to enter the non-masked regions by various means such as ion implantation, plasma immersion or diffusion from an applied surface film. If the modifier entry causes disruption of the silicon crystal structure (lattice damage), as in the case of ion implantation, then it is possible to measure the amount and profile of the damage as an indirect measure of the modifier itself. If damage is not caused, or in any case after the wafer is annealed to remove lattice damage and electrically activate the modifier material, then it is possible to measure the amount and profile of the activated dopant material, $D(x,y,z)$. This quantity is directly related to the electrical resistivity of the material which is very important technologically because it is a key parameter in the operation of the IC. This quantity also contains the "critical dimension" information pertaining to the ion implantation and annealing steps. An example is the important parameter, known as "junction depth" $(z_j)$, defined as the depth at which the activated dopant concentration falls off to a certain specified value (such as $10^{18}/cm^3$) that roughly equals the concentration of free carriers (of the opposite type) in the non-implanted regions of the wafer. More generally, $x_j$ and $y_j$ also similarly denote the lateral fall off of the dopant between doped and non-doped local regions.

There is considerable interest in analyzing the quality of the implant in a non-destructive optical manner. One such device that is commercially available to analyze implants is marketed by the assignee herein under the Therma-Probe trademark. This device includes an intensity modulated pump beam which is focused onto the sample surface. The pump beam creates both periodic heating and generates a periodic plasma which diffuses through the sample. The diffusion characteristics are directly effected by the damage to the lattice structure caused by the implantation step. The diffusion of the thermal and plasma components is monitored with a separate probe beam which is focused within the periodically excited area on the wafer. The probe beam monitors the periodic changes in reflectivity which are induced by the modulated thermal and plasma waves. Details of the basic physics and operation of a Therma-Probe device can be found in the following patents, each of which is incorporated by reference: U.S. Pat. Nos. 4,579,463; 4,636,088; 4,854,710 and 5,978,074.

The Therma-Probe device directly detects damage to the lattice structure of the crystalline structure of the wafer which then must be correlated with dose. It is believed that the subject scatterometry approach described herein may be able to analyze both the depth and lateral dimensions of an implant directly without correlation. The Therma-Probe is also generally limited to measurements in non-patterned regions of the wafer, while the subject scatterometry approach may be able to operate in a patterned areas on a die.

Other non-contact optical metrology tools have been used to measure compositional characteristics of semiconductor wafers. Ellipsometry and reflectometry are two examples of commonly used optical techniques. A reflectometer measures the change in intensity of a probe beam that reflects from the surface of the sample. An ellipsometer monitors the change in polarization state of a probe beam induced by interaction with the sample. Historically, these devices have been used to monitor compositional characteristics such as layer thickness, index of refraction and extinction coefficient. Examples of such tools are discussed in the following patents which are incorporated herein by reference: U.S. Pat. Nos. 5,608,526 and 5,798,837.

More recently, ellipsometric and reflectometric measurements have been used in the field of scatterometry. Scatterometry is a radiation metrology method for determining the shape and properties of a physical object that "scatters" the radiation. Here, "radiation" includes any wavelength ($\lambda$) of the electromagnetic spectrum. Generally the wavelengths used for a particular application are those that span the dimensions of the features or localized variations of the sample (wafer). For modern IC production and advanced development, the key circuit feature lateral dimension ($x_0$) range from 2000 nm (or $2 \times 10^{-6}$ meters) down to less than 50 nm. Ideally the wavelength range might extend from 10 $x_0$ to $\frac{1}{10} x_0$, but the practical reality is that a more limited wavelength range can perform successfully. Today the scatterometry wavelength range typically used is 800 nm down to the shortest wavelength conveniently available, which is about 190 nm.

The term "scatter", as in scatterometry, is a physics term meaning "to alter the propagation of a radiation wave". In general, the alteration may include refraction, reflection and diffraction. Each material causing the scatter may also have a nonzero part of the wavelength-dependent, complex refractive index $\tilde{n}(\lambda)$, leading to radiation absorption in addition to the above non-dissipative effects. Diffraction is present in all radiation propagation and scattering. However, to the extent that $x_0$ is less than the radiation wavelengths being employed in the scatterometry, then diffraction will play a stronger role in the scattering and the physical modeling must treat the diffraction component with increasing detail and accuracy for success.

Scatterometry generally employs an array of repetitive features in order to maximize the diffractive (constructive interference) component of the scattering. Simple line/space features (FIG. 2) are commonly employed currently. While most of the scatterometry studies have been directed to periodic line structures, these efforts have been extended to more complex 3D structures (e.g. vias) and even to isolated or aperiodic structures. The extension to non-periodic structures may require more complex mathematical modeling and a greater effort to maintain adequate signal-to-noise ratio in the apparatus but is nonetheless contemplated by this disclosure.

The basic diagram of a scatterometry system is shown in FIGS. 3a to 3c. Scatterometry may employ any of the following: an ellipsometric setup; a reflectometric setup; a range of incident wavelengths at one angle of incidence; one wavelength over a range of angles of incidence; both a range of wavelengths and a range of angles of incidence; or simply one wavelength and a single angle of incidence. These different setups result in different amounts of information content encoded onto the scattered light beam, resulting in different quality of detail and resolution in the desired extracted parameters. The preferred method that acquires the most information content, yet is practical for manufacturing use, is the broad-wavelength spectroscopic ellipsometer method, of rotating compensator design, at one angle of incidence. (See for example, U.S. Pat. No. 5,877,859, incorporated herein by reference.)

However, the application method disclosed here is independent of the details of the scatterometer apparatus design.

Additional background information on scatterometers and scatterometry analysis can be found in the following publications which are incorporated herein by reference. U.S. Pat. No. 5,607,800 (Ziger); U.S. Pat. No. 5,867,276 (McNeil); U.S. Pat. No. 5,739,909 (Blayo); U.S. Pat. No. 6,429,943 (Opsal); U.S. Pat. No. 6,483,580 (Xu); U.S. Pat. No. 2002/0038196 (Johnson) and U.S. Pat. No. 2002/0035455 (Niu).

As can be seen from the above citations, scatterometry has been proven capable of determining the cross-sectional shape of the line/space element of a repetitive array (grating) of IC features (such as the mask line/space in FIG. 2) which sit upon a substrate (such as the Si in FIG. 2). This technique has been applied to several IC processing steps including the photoresist develop-inspect step in lithography processing and the final-inspect step of etch processing.

It has recently been proposed that scatterometry system could be used to or monitor the ion implantation process. More specifically, U.S. Pat. No. 6,451,621, ('621 patent) incorporated herein by reference, notes that the implantation of dopants is controlled by an initial application of a photolithographic mask. As noted above, the mask often has grating-like properties in the active area of the wafer. Alternatively, the mask is often designed to provide test gratings in the inactive regions (scribe lines) of the wafer. The '621 patent proposes to measure the gratings of the mask using scatterometry. Since the mask is used to control the implant, accurate measurements of the mask can provide information about the dopants that will be implanted during the implantation step. It should be noted that the '621 patent only discloses measuring the mask prior to the implantation step as way to control or predict the implantation process.

The '621 patent does not disclose using scatterometry to actually measure the dopants after implantation.

U.S. Pat. No. 5,963,329 ('329 patent) also relates to scatterometry techniques for periodic structures. The '329 patent suggests that it might be possible to measure doping profiles using scatterometry. However, the '329 patent discloses a relatively complex and undesirable approach for carrying out the measurement. More specifically, the '329 patent suggests that it would be necessary to etch a grating structure into the wafer after the implantation step. The scatterometry tool would be used to measure the variations in the sidewalls of the grating in order to determine doping profiles. As can be appreciated, this approach requires an additional processing step in the wafer manufacture that would essentially destroy the wafer.

SUMMARY OF THE INVENTION

In accordance with the subject invention, it is proposed that a scatterometry measurement can be used to evaluate implantation parameters directly on a wafer without the need to create a separate grating into the doped material. More specially, we believe that scatterometry techniques can be employed to evaluate $M(x,y,z)$ and $D(x,y,z)$—and in addition $x_j$, $y_j$, and $z_j$—by applying a physical model to process the measured data and extract the desired information. It is believed that this approach can be used for both the pre-anneal and post anneal case. This approach can be used to determine the depth of junctions, particularly Ultra Shallow Junctions in very thin (<500 Angstroms) regions of the semiconductor.

In accordance with the subject method, the wafer is inspected with a scatterometry system after the implantation. The inspection can occur at one or more of a number of steps during the fabrication process. For example, the measurement can be made immediately after implantation while the mask it still on the semiconductor. Alternatively or in addition, the measurement can be made after the mask is removed. Again alternatively or in addition, the measurement can be made after the wafer has been annealed. The exact selection of timing and inspection parameters will be dependent on many factors including the time required, sensitivity before or after certain steps, etc. If multiple measurements are made, the results can be combined to improve the analysis.

Measurements made prior to anneal allow characterization of $M(x,y,z)$. Measurements made after anneal allow characterization of residual $M(x,y,z)$ (e.g., as a result of incomplete annealing) and of $D(x,y,z)$. Combination of the pre-anneal information with the post-anneal measurements may enable extraction of more information from the sample.

Further details of the subject invention will become apparent from the following detailed description taken in conjunction with the drawings in which:

DETAILED DESCRIPTION OF THE PREFERRED EMBODIMENTS

Figure 1:
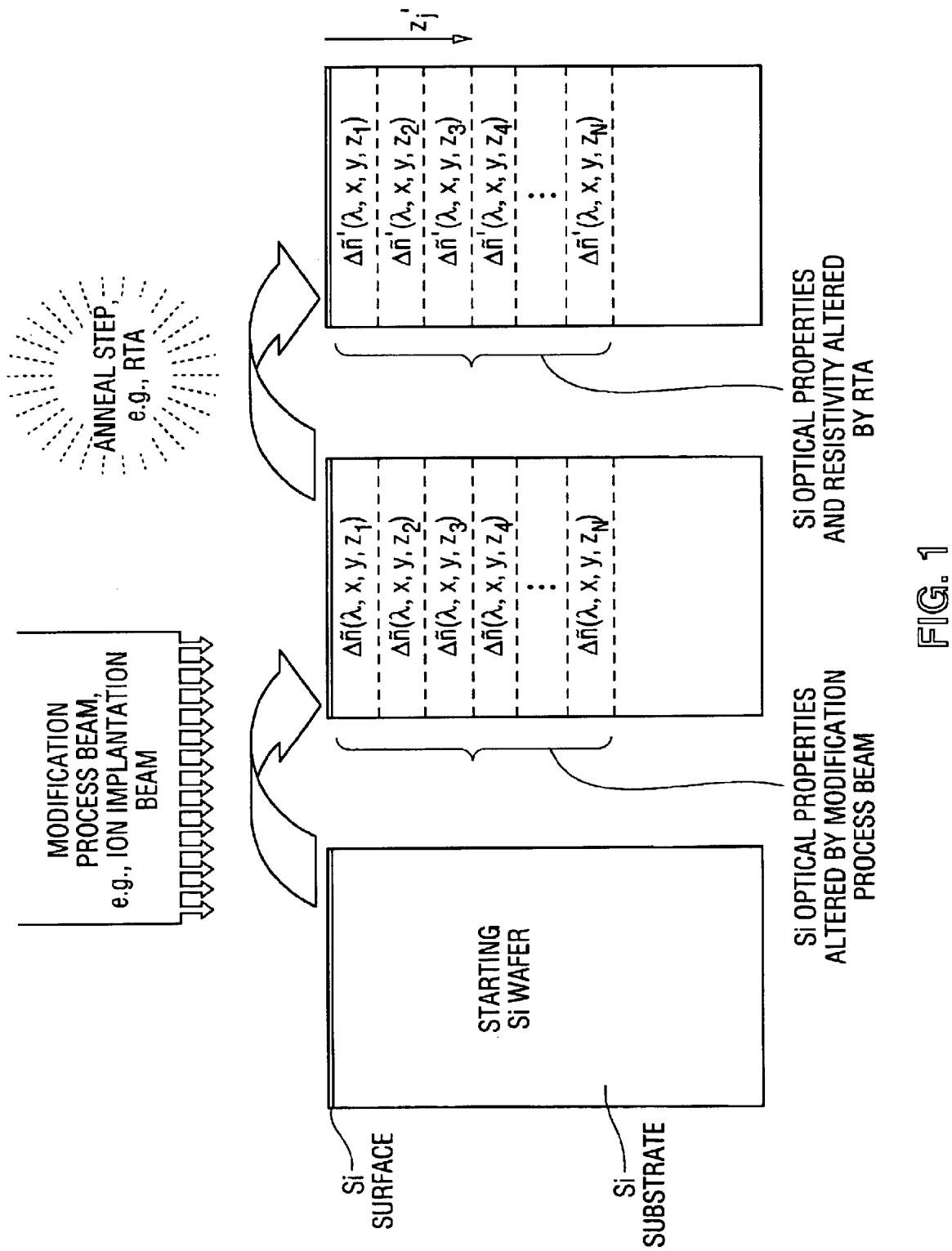
FIG. 1 is a schematic illustration of the formation of an electrical junction in a silicon wafer by ion implantation and rapid thermal annealing.

The subject method relates to the use of scatterometry for metrology of material doping processes. This disclosure includes (a) the employment of a mask (either a repetitive grating or a more general, partially-repetitive or non-repetitive design) to create an additional patterned modification in the material(s) underneath the mask caused by the IC processing which is desired to be characterized in the first place, and (b) the use of scatterometry involving the additional patterned modification to perform that characterization. This disclosure contemplates that, after the creation of the additional patterned modification, and before the scatterometry, the initial mask may or may not, optionally, be removed from the wafer, as will be described in detail below. The subject disclosure contemplates the determination by scatterometry of $M(x,y,z)$, $M_0(x,y)$, $D(x,y,z)$, $D_0(x,y)$, $x_j$, $y_j$, and $z_j$, and the post-anneal versions of these same quantities (defined below). In addition, it contemplates the determination of perturbations to the dimensional and optical properties of the initial mask (such as photoresist shrinkage), which also may have been modified by the IC process step.

In general, the concept here is to measure a wafer after implantation with a scatterometer device to gain insight into the implantation process. As set forth in the references cited above, a scatterometer can take many forms, all of which are intended to be covered by this disclosure. In all cases, at least one probe beam of light is directed to reflect off the sample. Preferably, polychromatic light is used and the reflected beam is monitored as a function of wavelength. In many current devices, only the zeroth order reflection is measured and based on that measurement, diffraction of light into the higher orders is inferred. Alternatively, higher diffraction orders can be measured.

Thus far, scatterometry has more typically been applied to 2D structures such as line gratings, but has recently been expanded to cover 3D structures such as a pattern of holes or vias as well aperiodic structures such as single lines. All of these techniques might be suitable for the approaches described herein.

In the simplest approach, the active semiconductor will have a periodic pattern of implanted regions which can be monitored by scatterometry. It is also well known that periodic reference patterns configured to optimize measurement can be formed in scribe lines on the wafer. In this case, the initial mask would be configured to place these reference patterns in the scribe lines. After implantation, scatterometry would be used to measure the implantation pattern in the region of the scribe lines. From these measurements, the character of the implantation in the active region can be inferred. In a more complex application, measurement in the active area of the IC device (not in the scribe line) can be achieved by the methods of this disclosure.

The analysis approaches will be similar to those described in the prior art. In the most basic approach, one can determine the scatterometry signature associated with a correct implant. Once the wafer to be tested is measured, the measured signal is compared to the scatterometry signal associated with a "good" wafer. If the signatures do not match, it is an indication that the implant did not go as planned.

It is also well known to create libraries of signatures associated with various possible geometries. A measured signaled can then be compared to the library to determine the nature of the implantation pattern.

It is also well known to make such analyses in real time. A mathematical model of the sample is created. A best guess of sample parameters is assigned to the model and the optical response of a structure having those selected parameters is calculated. Such calculations are performed using, for example, rigorous coupled wave theory or other frameworks such as Green's functions. (See, U.S. patent application Ser. No. 10/212385, filed Aug. 5, 2002 and incorporated herein by reference). The calculated optical response is compared to the measured optical response. Any deviations between the calculated optical response and the measured optical response are used to vary the initial starting parameter guesses and the process is repeated in an iterative fashion until satisfactory convergence is reached. Further information about real time analysis of periodic structures can be found in U.S. patent application Ser. No. 09/906290, filed Jul. 16, 2001 and incorporated herein by reference.

Set forth below are some possible applications and some examples for implementation.

Effect of Ion Implantation

Figure 2:
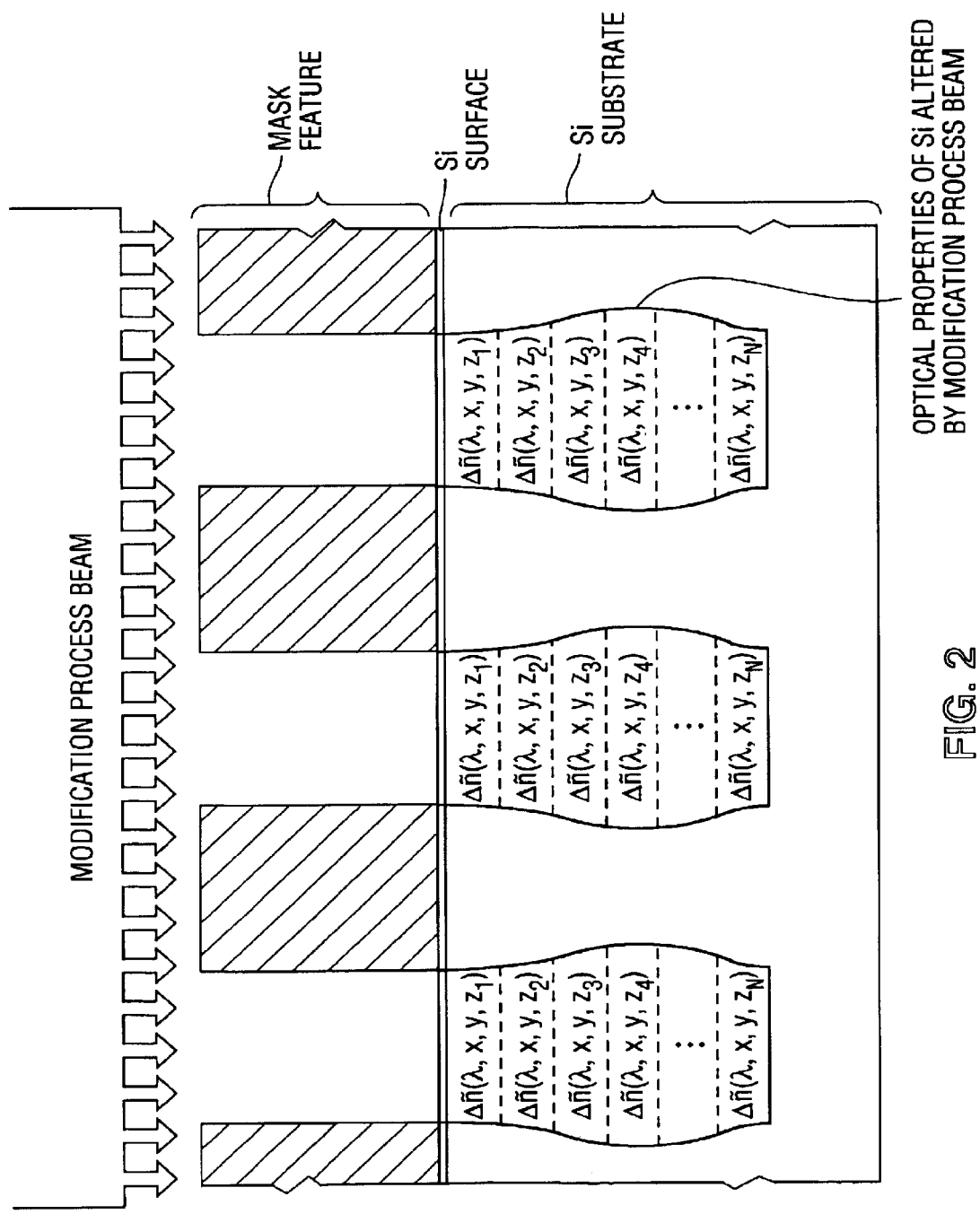
FIG. 2 is a schematic diagram of localized implantation using a periodic mask.
Figure 3A:
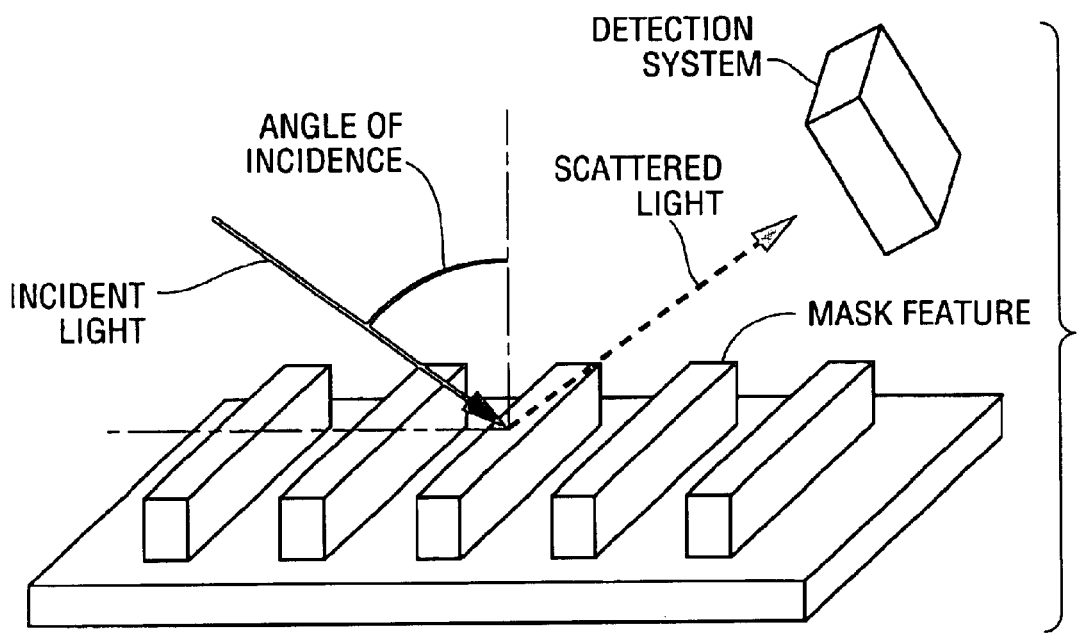
FIG. 3a is schematic diagram of a basic scatterometry measurement system in perspective.
Figure 3B:
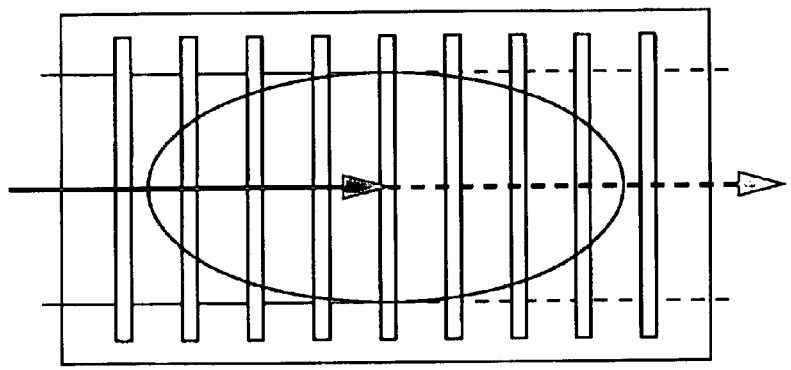
FIG. 3b is a top view thereof and FIG. 3c is a side view thereof.
Figure 3C:
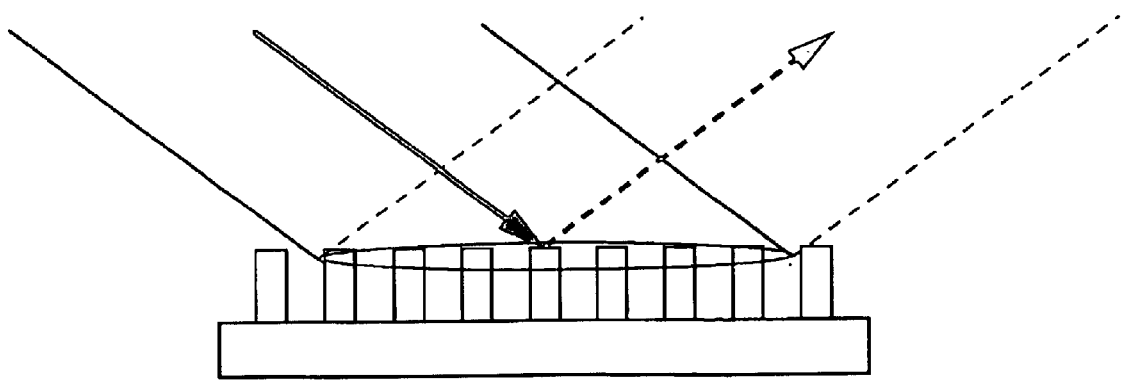

The purpose of ion implantation in Ultra Shallow Junction (USJ) formation is to inject the correct dose of ions of the correct atomic number at the correct depth(s) in the silicon. Denote the complex refractive index of the silicon material by $\tilde{n}(\lambda)$. Then in the regions between the mask lines (FIG. 2), the ion implantation step will alter $\tilde{n}$ by a certain amount (denoted $\Delta\tilde{n}$, or more completely, $\Delta\tilde{n}(\lambda)$). Since the depth of the ion implantation is limited by the energy of the ion beam, and the lateral extent of the ion implantation is also limited (by the mask and by transverse straggle of the ion beam), $\Delta\tilde{n}$ is also a function of x, y, and z, as indicated in FIG. 2. $\Delta\tilde{n}$ can be determined by scatterometry using one the approaches set forth above. The generally high sensitivity of scatterometry to the shape of this spatially-periodic modification is an advantage of the method disclosed here compared to all previous methods of nondestructively measuring $\Delta\tilde{n}(x,y,z)$ and hence extracting $M(x,y,z)$, $M_0(x,y)$, $D(x,y,z)$, $D_0(x,y)$, and $x_j$, $y_j$, $z_j$.

Effect of Rapid Thermal Anneal

The purpose of the rapid thermal anneal (RTA) process is to restore perfection to the Si crystal lattice and allow the implanted ions to move to lattice sites which enable activation of their additional charge carriers (electrons or holes). To the extent that the RTA creates too low a temperature in the wafer, the implant damage may not be adequately removed, inhibiting carrier activation and damaging IC performance. To the extent that the RTA creates too high a temperature in the wafer, or holds the temperature high for too long a time, the implanted ions may diffuse too far from the implanted location, resulting in reduced conductivity at the desired location, or otherwise, and degrading the IC performance. As discussed in more detail below, and in accordance with the subject invention, such variations can be monitored using scatterometry.

Specific Examples

Figure 4:
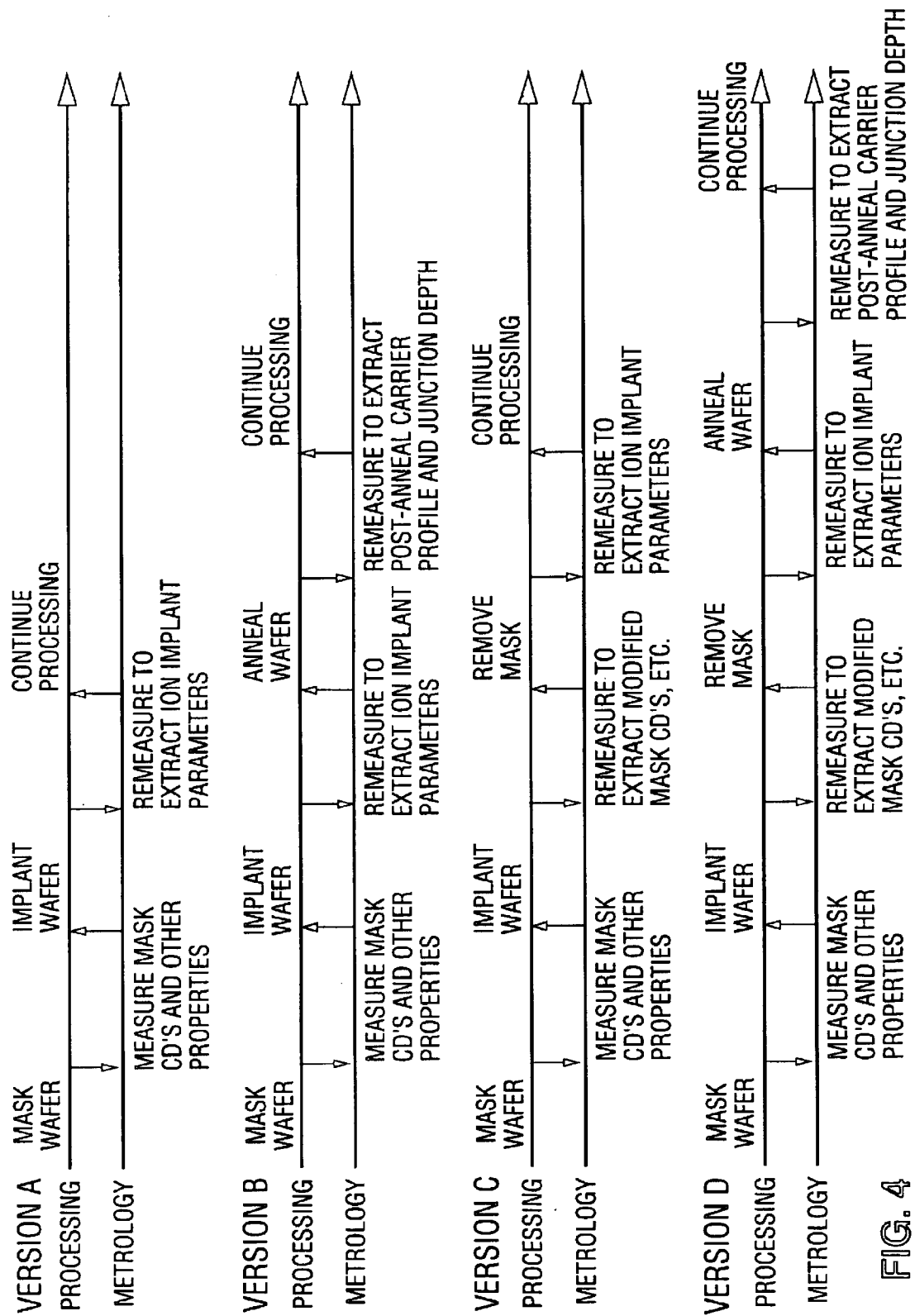
FIG. 4 is a process flow diagram illustrating variations of the subject invention.

Some specific examples of the subject method will be discussed with reference to FIG. 4. The methods disclosed herein may be one-step or two-step, each with a pre-anneal and a post-anneal variant.

As noted above, the subject invention is intended to cover a measurement of an implanted region via scatterometry. The following specific methodologies are more specific and provided as exemplary only and not limiting the scope of the claims.

Version A. The one-step, pre-anneal method would involve the following sequence of steps: prepare the wafer through the masking process, measure the wafer in the scatterometry apparatus to characterize the mask critical dimensions and fix certain variables (such as the mask feature pitch, mask feature height, etc.) to reduce the number of fitted parameters in the next steps, implant the wafer, remeasure wafer in the scatterometry apparatus, model the entire structure (mask and silicon), extract $\Delta \tilde{n}(x,y,z)$, convert $\Delta \tilde{n}(x,y,z)$ to the desired outputs such as $M(x,y,z)$ or $M_0(x,y)$, and optionally to further convert by calibration or modeling to dose. Any significant perturbation of the mask features themselves by the ion implantation must be included in the modeling or added as a correction step at the end.

Version B. The one-step, post-anneal method involves the same sequence of steps as above, followed by the additional step of the anneal and then remeasurement of the wafer in the scatterometry apparatus, model the entire structure (mask and silicon), extract $\Delta \tilde{n}'(x,y,z)$, convert $\Delta \tilde{n}'(x,y,z)$ to the desired outputs such as residual (post anneal) damage $M'(x,y,z)$, $M'_0(x,y)$, $D'(x,y,z)$, $D_0'(x,y)$, or $x_j'$, $y_j'$, $z_j'$. Here, the ' symbol explicitly denotes post-anneal parameters. $Z_j'$ is the conventional junction depth. The residual (post anneal) damage parameters $M'(x,y,z)$ and $M'_0(x,y)$, as well as $x_j'$, $y_j'$ and $z_j'$, are key parameters for maintaining process quality on the anneal step. Modern rapid anneal process has difficulty controlling the maximum temperature experienced by the wafer in the production line, resulting in undesired variation in $M'(x,y,z)$, $M'_0(x,y)$, $D'(x,y,z)$, $D_0'(x,y)$, $x_j'$, $y_j'$, or $z_j'$. A benefit of the method disclosed here is the potential improvement in the process control of the rapid anneal step and resulting wafer quality.

Version C. The two-step pre-anneal version would insert an extra step of removing the mask layer after the ion implantation step. The benefit of this removal is that some variables would have been determined in the initial scatterometry step (such as the mask pitch) and fixed for the final scatterometry measurement, and there are fewer shape parameters to be fitted in the final scatterometry, resulting in better precision. The sequence would be as follows: First, prepare the wafer through the masking process, measure the wafer in the scatterometry apparatus to characterize the mask critical dimensions and fix certain variables (mask feature pitch, mask feature height, etc.) to reduce the number of fitted parameters in the next steps, implant the wafer, remove the mask by plasma or wet etching, remeasure the wafer in the scatterometry apparatus, model the simpler structure (silicon only, no mask), extract $\Delta \tilde{n}(x,y,z)$, convert $\Delta \tilde{n}(x,y,z)$ to the desired outputs such as $M(x,y,z)$ or $M_0(x,y)$, and optionally to further convert by calibration or modeling to dose. Any significant perturbation of the mask features themselves by the ion implantation would not be measured in this case, and could lead potentially to some error in the outputs. This could be addressed by performing a scatterometry step after the ion implantation but before the mask removal to include characterization of the change in the mask induced by the ion implantation.

Version D. The two-step version, post-anneal version would similarly insert the extra mask-removal step into the sequence described previously for the one-step, post-anneal version.

Note that a portion of any one of the sequences described above may also be useful as a production monitor method employing scatterometry for ion implantation and USJ control.

It is also contemplated to use ion implant simulation code such as TRIM or Supreme, etc., in combination with the mask geometry information to calculate the z-dependence of the damage and the lateral straggle of the ion implantation into the $S_i$. This shape information may be useful in the extraction of $\tilde{n}(x,y,z)$ or conversion of that into $D_0(x,y)$.

Comprehensive Production Control of USJ Formation

The method disclosed here is capable of characterizing in one metrology system both critical aspects of the USJ process—ion implantation and RTA.

First, the subject method measures the dose and depth profile of the ion implantation in the actual sub-micron-scale patterned features, and can provide contour maps of uniformity across the wafer. These outputs protect the USJ from process errors including operator error and equipment malfunctions. Equipment malfunctions include a variety of effects that degrade IC performance uniformity across the wafer. Nonuniformities may arise from ion beam scan distortion, ion dose nonuniformity, ion beam energy nonuniformity, ion beam contamination, etc. The subject method can be used at this point in the manufacturing process to certify that the ion implantation section of the USJ formation was successful.

Next, the subject method characterizes the RTA process in several key respects. If the RTA temperature/time is too low, then $\Delta \tilde{n}(x,y,z)$—the measured modification of the optical properties of the implanted Si regions—reveals the existence of excessive residual damage due to certain spectral features in the real or imaginary part of $\Delta \tilde{n}(x,y,z)$. These features can be used as a process control method for damage removal. If the RTA temperature/time is excessive, the subject method can detect the reduction in the carrier concentration at the desired shallow depth in the silicon and the increased carrier concentration at deeper depths. Third, the subject method can reveal RTA nonuniformities (such as lamp nonuniformity, lamp failure, control failure) across the wafer via contour maps. Methods to characterize and maintain production control of USJ formation are highly valuable in modern IC manufacturing.

While the subject invention has been described with reference to some preferred embodiments, various changes and modifications could be made therein, by one skilled in the art, without varying from the scope and spirit of the subject invention as defined by the appended claims

I claim:

1. A method of fabricating a semiconductor wafer comprising the steps of:

implanting dopants in one or more regions below the surface of the wafer, a mask having previously been applied to the wafer to control the location at which the dopants will be implanted;

making a first inspection of the surface of the wafer with a scatterometer after the mask has been applied but before the dopants have been implanted;

making a second inspection of the surface of the wafer with a scatterometer after the dopants have been implanted; and analyzing the output from the first and second inspection steps of the scatterometer to evaluate the characteristics of the dopants in the wafer.

2. A method of fabricating a semiconductor wafer comprising the steps of:

implanting dopants in one or more regions below the surface of the wafer;

inspecting the surface of the wafer with a scatterometer;

analyzing the output of the scatterometer to evaluate the characteristics of the dopants in the wafer; and annealing the wafer after the implantation of the dopants but prior to the inspection with the scatterometer.

3. A method of fabricating a semiconductor wafer comprising the steps of:

implanting dopants in one or more regions below the surface of the wafer;

inspecting the surface of the wafer with a scatterometer;

analyzing the output of the scatterometer to evaluate the characteristics of the dopants in the wafer; and annealing the wafer after implantation and after the inspection step and further including the step of inspecting the surface of the wafer with a scatterometer after the annealing step and analyzing the output from both the inspection steps of the scatterometer to evaluate the characteristics of the dopants in the wafer.

4. A method of evaluating dopants implanted under the surface of a semiconductor wafer, comprising the steps of:

illuminating the surface of the wafer with a probe beam of radiation;

monitoring the probe beam after reflection from the wafer and analyzing changes in the intensity or polarization state of the beam and generating output signals in response thereto; and comparing the measured signals to calculated signals, said calculated signals being generated by applying a scatterometry analysis to a theoretical model having theoretical parameters associated with the wafer under test in order to evaluate the dopants in the wafer under test, said calculated signals being in the form of a library of signals calculated using a plurality of sets of different theoretical parameters applied to the model and wherein the comparison step attempts to most closely match the measured signals to a set of calculated signals stored in the library.

5. A method of evaluating dopants implanted under the surface of a semiconductor wafer, comprising the steps of:

illuminating the surface of the wafer with a probe beam of radiation;

monitoring the probe beam after reflection from the wafer and analyzing changes in the intensity or polarization state of the beam and generating output signals in response thereto; and comparing the measured signals to calculated signals, said calculated signals being generated by applying a scatterometry analysis to a theoretical model having theoretical parameters associated with the wafer under test in order to evaluate the dopants in the wafer under test, wherein said comparison step is repeated in an iterative analysis where the theoretical parameters of the model are iteratively adjusted so that the difference between the calculated theoretical signals and the measured signals is minimized.

6. The method of claim 4, wherein the location of the implanted dopants was controlled by the prior application of a lithographic mask and wherein the illuminating and monitoring steps are performed prior to the removal of the mask.

7. The method of claim 4, wherein the location of the implanted dopants was controlled by the prior application of a lithographic mask and wherein the illuminating and monitoring steps are performed after the mask is removed.

8. A method of evaluating dopants implanted under the surface of a semiconductor wafer, comprising the steps of:

illuminating the surface of the wafer with a probe beam of radiation;

monitoring the probe beam after reflection from the wafer and analyzing changes in the intensity or polarization state of the beam and generating output signals in response thereto; and comparing the measured signals to calculated signals, said calculated signals being generated by applying a scatterometry analysis to a theoretical model having theoretical parameters associated with the wafer under test in order to evaluate the dopants in the wafer under test;

wherein the location of the implanted dopants was controlled by the prior application of a lithographic mask and wherein the illuminating and monitoring steps are performed prior to the removal of the mask; and wherein the steps of illuminating and monitoring are also performed after the mask has been applied but before the dopants have been implanted and wherein the output signals from both monitoring steps are analyzed to evaluate the characteristics of the dopants in the wafer.

9. A method of evaluating dopants implanted under the surface of a semiconductor wafer, comprising the steps of:

illuminating the surface of the wafer with a probe beam of radiation;

monitoring the probe beam after reflection from the wafer and analyzing changes in the intensity or polarization state of the beam and generating output signals in response thereto; and comparing the measured signals to calculated signals, said calculated signals being generated by applying a scatterometry analysis to a theoretical model having theoretical parameters associated with the wafer under test in order to evaluate the dopants in the wafer under test;

wherein the location of the implanted dopants was controlled by the prior application of a lithographic mask and wherein the illuminating and monitoring steps are performed after the mask is removed; and wherein the steps of illuminating and monitoring are also performed after the mask has been applied but before the dopants have been implanted and wherein the output signals from both monitoring steps are analyzed to evaluate the characteristics of the dopants in the wafer.

10. A method of evaluating dopants implanted under the surface of a semiconductor wafer, comprising the steps of:

illuminating the surface of the wafer with a probe beam of radiation;

monitoring the probe beam after reflection from the wafer and analyzing changes in the intensity or polarization state of the beam and generating output signals in response thereto;

comparing the measured signals to calculated signals, said calculated signals being generated by applying a scatterometry analysis to a theoretical model having theoretical parameters associated with the wafer under test in order to evaluate the dopants in the wafer under test; and annealing the wafer after the implantation of the dopants but prior to the illuminating and monitoring steps.

11. A method of evaluating dopants implanted under the surface of a semiconductor wafer, comprising the steps of:

illuminating the surface of the wafer with a probe beam of radiation;

monitoring the probe beam after reflection from the wafer and analyzing changes in the intensity or polarization state of the beam and generating output signals in response thereto;

comparing the measured signals to calculated signals, said calculated signals being generated by applying a scatterometry analysis to a theoretical model having theoretical parameters associated with the wafer under test in order to evaluate the dopants in the wafer under test; and annealing the wafer after implantation and after the illuminating and monitoring steps and wherein the steps of illuminating and monitoring are also performed after the annealing step and wherein the output signals from both monitoring steps are analyzed to evaluate the characteristics of the dopants in the wafer.

12. The method of claim 1, wherein said second inspection step is carried out prior to the removal of the mask.

13. The method of claim 1, wherein said second inspection step is carried out after the mask is removed.

* * * * *